United States Patent
Trate et al.

[19]

[11] Patent Number: 5,877,427
[45] Date of Patent: Mar. 2, 1999

[54] WEATHERSTRIP RESILIENCY TEST FIXTURE

[75] Inventors: Daryl J. Trate, West Bloomfield; Randy L. Dickerman, Ypsilanti; Peter Polasek, Grosse Pointe, all of Mich.

[73] Assignee: Chrysler Corporation, Auburn Hills, Mich.

[21] Appl. No.: 885,037

[22] Filed: Jun. 30, 1997

[51] Int. Cl.$^6$ ................................................. G01L 1/024
[52] U.S. Cl. ................................................. 73/800; 73/823
[58] Field of Search .................... 73/781, 788, 790, 73/800, 818, 822, 823

[56] References Cited

U.S. PATENT DOCUMENTS

| 4,667,095 | 5/1987 | Hatanaka et al. | 73/800 |
|---|---|---|---|
| 4,690,001 | 9/1987 | Harvey et al. | 73/800 |
| 4,939,368 | 7/1990 | Brown | 73/800 |
| 5,199,304 | 4/1993 | Ferguson | 73/800 |

*Primary Examiner*—Max H. Noori

[57] ABSTRACT

A fixture for testing the resiliency of vehicle bulb-type weatherstripping before and after the weatherstripping has been heat treated includes a base and a holder movably positioned on the base for holding the weatherstripping. A ram is movably disposed on the base opposite the holder for motion between a compressed position, wherein the ram abuts the weatherstripping to compress the weatherstripping, and a release position, wherein the ram is distanced from the weatherstripping. A laser device is positioned for directing laser light onto the weatherstripping as it recovers from a compressed configuration to a relaxed configuration. As the weatherstripping recovers, the laser light is reflected off of the weatherstripping, detected, and a detection voltage is correlated to a distanced moved by the weatherstripping as a function of time. Thereby, a measure of the resiliency and recoverability of the weatherstripping is provided.

17 Claims, 2 Drawing Sheets

5,877,427

WEATHERSTRIP RESILIENCY TEST FIXTURE

FIELD OF INVENTION

The present invention relates generally to systems for assuring the quality of vehicles, and more particularly to apparatus for testing the resiliency and recoverability of vehicle weatherstripping.

BACKGROUND OF THE INVENTION

Weatherstripping is resilient material that is used in vehicles to establish a seal between two metal, plastic, or other components that can move relative to each other, e.g., between a door and a door frame of the vehicle. In many current applications, the weatherstripping is configured as a hollow tube of rubber or other resilient material (referred to as a "bulb-type" seal) that is attached to one of the metal components and that is compressed between the two metal components when the components are closely engaged, e.g., when a door is shut against its associated door frame.

As recognized herein, it is important that the weatherstripping retain sufficient resiliency so that the weatherstripping adequately rebounds after being repeatedly compressed and relaxed, to ensure that the weatherstripping continues to establish an acceptable air aspiration, dust, and fluid seal between its associated metal components. It is also important that the weatherstripping retain its resiliency after being exposed to heat for long periods. The present invention further recognizes that the above consideration implies the desirability of testing specimens of the weatherstripping material after they have been compressed while being heated to simulate a hostile environment, both to ensure that the material characteristics of the weatherstripping is satisfactory, and to compare and contrast various types of weatherstripping.

With the above considerations in mind, we understand that it is desirable to test the resiliency of samples of actual bulb-type weatherstripping samples. Existing test fixtures, however, cannot accurately test weatherstripping material with much reliability and repeatability. Accordingly, we have recognized the need to provide a fixture for accurately testing bulb-type weatherstripping samples of production weatherstripping.

It is therefore an object of the present invention to provide a fixture and method for accurately testing material characteristics of vehicle weatherstripping, and evaluating the design thereof. Another object of the present invention is to provide a fixture and method for accurately testing material characteristics of vehicle weatherstripping that is configured as bulb-type weatherstripping. Still another object of the present invention is to provide a fixture and method for accurately testing material characteristics of vehicle weatherstripping that is easy to use and cost-effective to manufacture.

SUMMARY OF THE INVENTION

A fixture for testing vehicle weatherstripping includes a base and a holder on the base for mounting the weatherstripping. The holder is movable on the base. A ram is movably disposed on the base opposite the holder for motion between a compressed position, wherein the ram abuts the weatherstripping to compress the weatherstripping, and a release position, wherein the ram is distanced from the weatherstripping.

In a preferred embodiment, a laser device is positioned for directing laser light onto the weatherstripping and for receiving reflected laser light therefrom. In this embodiment, an electric circuit including a microprocessor is electrically connected to the laser device for correlating the reflected laser light to the distance through which the specimen moved while recovering from compression. Desirably, the laser device is engageable with at least one pin coupled to the base, such that the laser device is easily removed from the base to facilitate heating the base with the ram in the compressed position to treat the weatherstripping prior to testing it.

Per the preferred embodiment, the ram includes a ram support that is fixedly attached to the base, and the ram support includes at least one ram support rod. A ram element is slidably engaged with the ram support rod for establishing the compressed position and the release position. Moreover, the ram includes a spring coupled to the ram support and to the ram element to pull the ram element toward the release position. As intended by the present invention, a trigger is pivotably mounted on the base and is engageable with the ram element for selectively holding the ram element in the compressed position. Additionally, a lock is engaged with the trigger, and the lock can be moved relative thereto for selectively holding the trigger in engagement with the ram element.

In addition to the preferred ram structure disclosed above, the preferred holder structure includes a horizontal holder member that is movably disposed relative to the base for moving horizontally toward and away from the ram. Also, the holder includes a vertical holder member that is movably disposed relative to the horizontal holder member for vertical motion relative thereto. A bracket is attached to one of the holder members for engaging the weatherstripping. Horizontal and vertical micrometers are respectively engaged with the horizontal and vertical holder members and are manipulable by a person for selectively moving the bracket horizontally and vertically, respectively, relative to the base.

In another aspect of the present invention, a method for testing the resiliency of a specimen of vehicle weatherstripping includes movably disposing the specimen on a base and compressing the specimen. Further, the method includes juxtaposing a laser with the specimen such that the laser can direct laser light against the specimen. Moreover, the method includes releasing the specimen, and then detecting laser light reflected from the specimen to detect movement of the specimen.

In yet another aspect, a fixture for determining the resiliency of a specimen of vehicle weatherstripping includes a holder attachable to the specimen and movably disposed on a base. A ram is movably disposed on the base opposite the holder, with the ram being movable to a compressed position, wherein the ram squeezes the specimen against the holder to move the specimen to a compressed configuration. Also, the ram is biased to a release position, wherein the ram is distanced from the specimen and the specimen is not compressed against the holder. A laser device is positioned to illuminate the specimen with laser light and to detect reflections therefrom.

In still another aspect of the present invention, a computer program product is disclosed which is readable by a digital processing apparatus and which tangibly embodies a computer program. The computer program product combines a computer readable medium with program code elements that determine the resiliency of a specimen of vehicle weatherstripping. The computer usable code means have computer readable code means for receiving digitized voltage signals from a laser light detector, it being understood that the voltage signals are generated in response to the specimen moving from a compressed configuration to a relaxed configuration. Computer readable code means are provided for correlating the voltage signals to a distance displaced by the specimen as it moves from the compressed configuration to the relaxed configuration.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

This invention measures the resiliency of a specimen of vehicle bulb-type weatherstripping, using laser technology, as the weatherstripping recovers from a compressed configuration to a relaxed configuration. Thereby, the present invention provides a system for reliably measuring, with a high degree of repeatability, how well a particular type of weatherstripping retains it resiliency after, e.g., being heat treated. Such heat treatment simulates hot weather conditions which can cause vehicle weatherstripping to lose its resiliency and, thus, its sealing properties. Further, the invention evaluates the weatherstripping material's ability to follow the flexing of a sealing surface.

Figure 1:
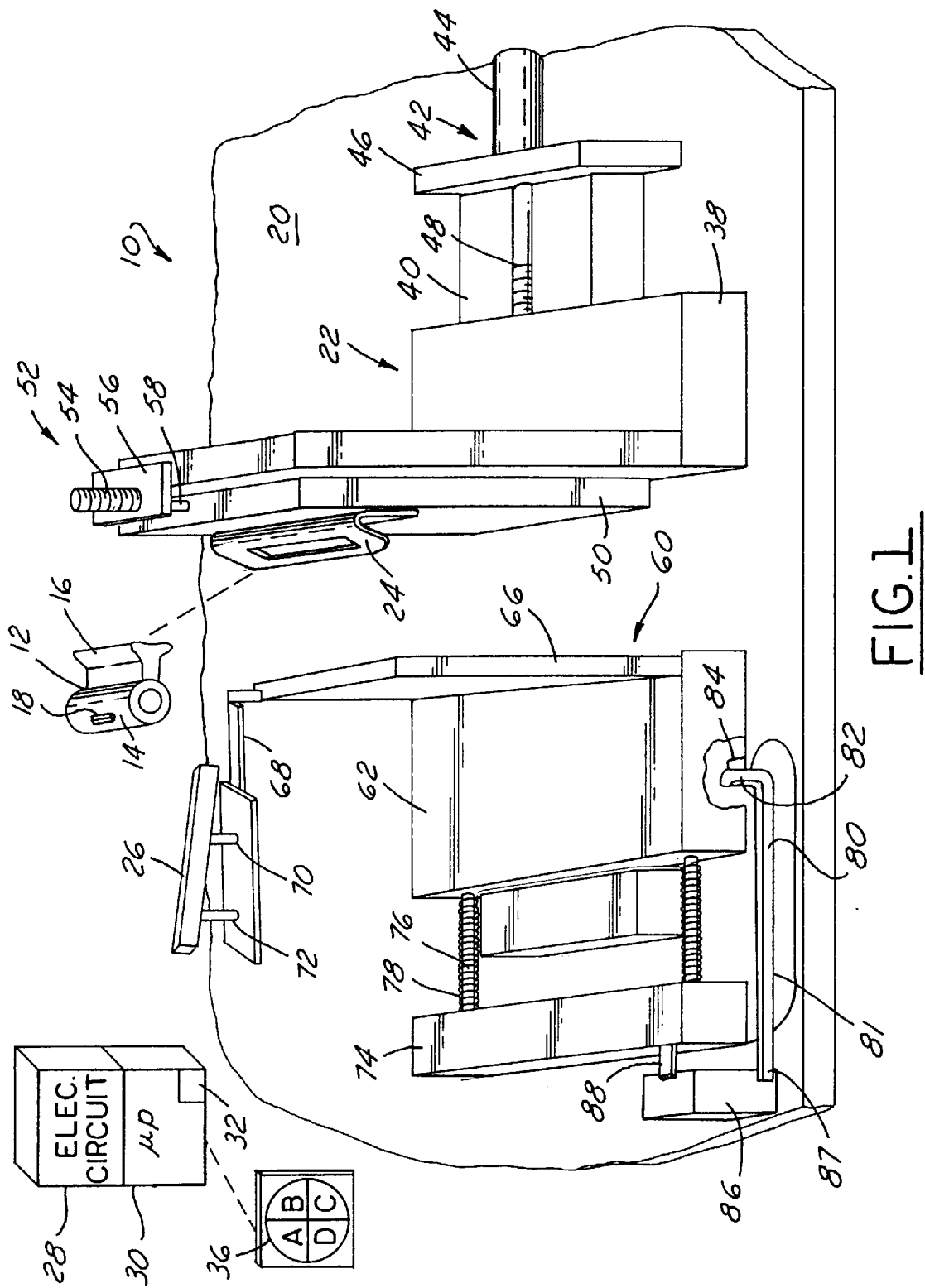
FIG. 1 is a perspective view of the weatherstrip test fixture, showing a test specimen in an exploded relationship therewith and showing portions of the test table broken away for clarity, and further showing the program storage device schematically.

Referring initially FIG. 1, a test fixture, generally designated 10, is shown for testing a hollow, resilient, rubber or plastic bulb-type weatherstrip specimen 12 having a hollow compressible seal segment 14 and a solid flange segment 16 configured generally triangularly in transverse cross-section. A layer 18 of laser-reflective paint is deposited on the seal segment 14 for purposes to be shortly disclosed. Preferably, the layer 18 is made of a nitrile latex paint.

A rigid base 20 supports a holder, generally designated 22, with the holder 22 including a slotted bracket 24 configured for closely receiving the flange segment 16 of the specimen 12. As can be appreciated in reference to FIG. 1, a laser device 26 can be positioned to direct laser light against the layer 18 and to receive reflections of laser light therefrom. Accordingly, the laser device 26 includes both a source of laser light and a laser light detector. In the presently preferred embodiment, the laser device 26 is a type LB-60 laser device made by Keyence of Japan that has a twenty millisecond response speed and that can support obtaining twenty five hundred (2500) readings per test interval.

For purposes to be more fully disclosed below, an electrical circuit 28 with associated microprocessor 30 receive the output of the laser device 26. The microprocessor 30 can be a Pentium® based laptop or personal computer 12 that includes a resiliency evaluation module 32 which may be executed by a processor within the microprocessor 30 as a series of computer-executable instructions. These instructions may reside, for example, in RAM of the microprocessor 30.

Alternatively, the instructions may be contained on a data storage device with a computer readable medium, such as a computer diskette 34 shown in FIG. 1. Or, the instructions may be stored on a DASD array, magnetic tape, conventional hard disk drive, electronic read-only memory, optical storage device, or other appropriate data storage device. In an illustrative embodiment of the invention, the computer-executable instructions may be lines of compiled $C^{++}$ language code.

Figure 4:
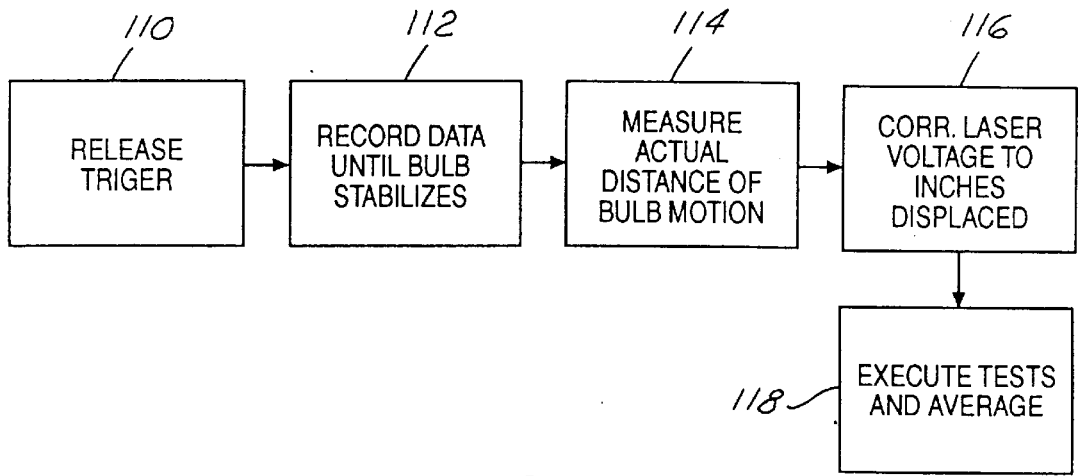
FIG. 4 is a flow chart of the logic used by the present invention.

FIG. 4 illustrates the structure of such instructions as embodied in a computer program. Those skilled in the art will appreciate that FIG. 4 illustrates the structures of computer program code elements that function according to this invention. Manifestly, the invention is practiced in its essential embodiment by a machine component that renders the computer program code elements in a form that instructs a digital processing apparatus (that is, a computer) to perform a sequence of function steps corresponding to those shown in the Figures. The machine component is shown in FIG. 1 as a combination of program code elements A–D in computer readable form that are embodied in a computer-usable data medium 36, on the computer diskette 34. As mentioned above, however, such media can also be found in semiconductor devices, on magnetic tape, and on optical disks.

The details of the fixture 10 will now be described in reference to FIG. 1. Beginning with the holder 22, a rigid horizontal holder member 38 is movably disposed on the base 20 for moving horizontally over the base 20. Preferably, the horizontal holder member 38 is formed with a central parallelepiped-shaped channel that closely slidably engages a complementarily-shaped guide rail 40, on the base 20. Like the base 20 and the other mechanical components of the fixture 10, the horizontal member 38 and rail 40 can be made of rigid hard metal or plastic.

To move the horizontal holder member 38 relative to the base 20, a horizontal micrometer, generally designated 42, includes a handle 44 that is rotatably engaged with a horizontal mount 46 on the base 20. As can be appreciated in reference to FIG. 1, the handle 44 is rotatable by a person for rotating a micrometer shaft 48, with the shaft 48 being engaged with the horizontal holder member 38 for translating rotational motion of the handle 44 to translational motion of the member 38 in accordance with well-known micrometer principles. In further accordance with well-known micrometer principles, a person can determine the relative translational position of the horizontal holder member 38 relative to the base 20 by observing the score lines on the handle 44 of the horizontal micrometer 42.

Additionally, a vertical holder member 50 is slidably engaged with the horizontal holder member 38 for up and down motion of the vertical holder member 50 relative to the horizontal holder member 38. To move the vertical holder member 50 relative to the horizontal holder member 38, a vertical micrometer, generally designated 52, includes a handle 54 that is rotatably engaged with a vertical mount 56 on the horizontal holder member 38. As can be appreciated in reference to FIG. 1, the handle 54 of the vertical micrometer 50 is rotatable by a person for rotating a micrometer shaft 58. It is to be understood that in all other essential respects, the vertical micrometer 50 is identical in construction and operation to the horizontal micrometer 38, such that the relative translational position of the vertical holder member 50 with respect to the horizontal holder member 38 is indicated the score lines on the handle 54 of the vertical micrometer 50.

FIG. 1 shows that the bracket 24 is fixedly attached to the vertical holder member 50 for engaging the weatherstripping specimen 12 with the holder 22. To compress the specimen 12 against the holder 22, a ram, generally designated 60, is movably disposed on the base 20 opposite the holder 22 for motion between a compressed position, wherein the ram 60 abuts the weatherstripping specimen 12 to compress the weatherstripping specimen 12 against the holder 22, and a release position, wherein the ram 60 is distanced from the specimen 12.

In the preferred embodiment, the ram 60 includes a ram base 62 that is slidably engaged with a parallelepided-shaped ram rail 64 on the base 20. Also, the ram 60 includes a ram wall 66 that rises from the ram base 62 and that contacts the specimen 12 to move the specimen 12 to a compressed configuration when the ram 60 is in the compressed position. A laser mounting platform 68 is connected to the top of the ram wall 66 as shown, and the mounting platform includes two vertically-oriented cylindrical pins 70, 72 that are slidably received into complementarily-configured receptacles on the laser device 26, to thereby removably hold the laser device 26 on the ram 60. In this way, the laser device 26 can be easily removed from the base 20 to facilitate heat treating the specimen 12 on the base 20 with the ram 60 in the compressed position, without also undesirably heating the laser device 26.

With respect to further details of the ram 60, the ram 60 is spring biased to the release position, wherein the ram 60 is distanced from the holder 22. Specifically, a ram support 74 includes cylindrical ram support rods 76 that are slidably engaged with the ram base 62, and the ram support 74 is fixedly attached to the base 20. Respective springs 78 surround the rods 76 and are affixed to the ram support 74 and to the ram base 62 in tension to pull the ram base 62 away from the holder 22, i.e., toward the release position.

To hold the ram 60 in the compressed position, an elongated rigid trigger 80 is pivotably mounted on the base 20 by means of a pivot pin 81, and the trigger 80 is engageable with the ram base 62. More particularly, the trigger 80 includes an engagement abutment 82 that rises upwardly to contact a trigger stop 84 on the ram base 62 as shown, when the ram 60 is in the compressed position, to thereby prevent the ram 60 from returning to the release position. A lock 86 is rotatably engaged with the trigger 80 by means of a lock pin 87 as shown, and the lock 86 can be moved relative to the trigger 80 into the orientation shown in FIG. 1 to abut a lock stop 88 on the ram support 74 to thereby hold the trigger 80 in engagement with the ram base 62. When the lock 86 is rotated away from the lock stop 88, the trigger 80 can be pivoted away from the pivot stop 84 to thereby release the ram base 62, such that the springs 78 can pull the ram base 62 away from the holder 22, to the release position.

Figure 2:
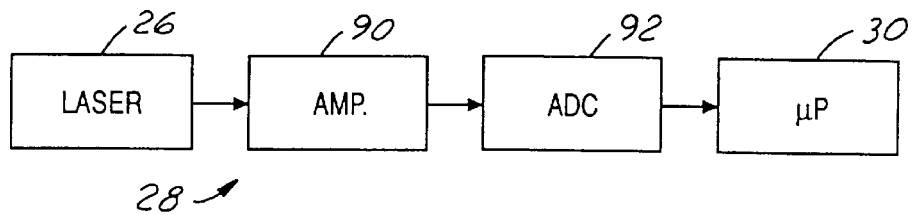
FIG. 2 is a block diagram of the electrical components of the present invention.

Referring briefly to FIG. 2, the electronic circuit 28 includes an amplifier 90 which amplifies the output from the laser device 26. The amplified output is then digitized by an analog to digital converter (ADC) 92, and then sent to the microprocessor 30.

Figure 3:
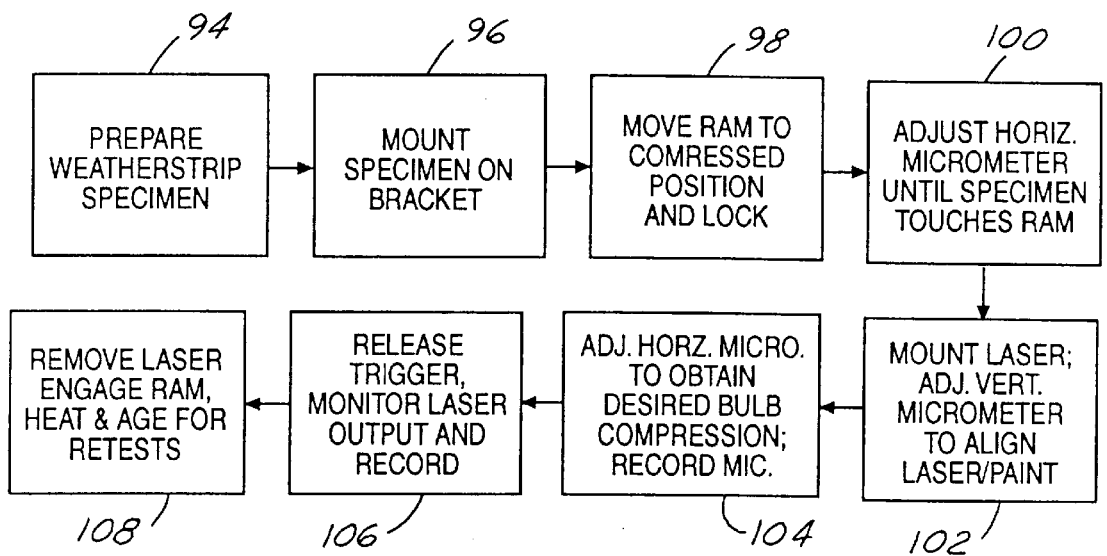
FIG. 3 is a block diagram showing the method steps of the present invention.

With the above cooperation of structure in mind, the operation of the fixture 10 can be understood in reference to FIG. 3. At block 94, the specimen 12 is prepared by cutting the specimen 12 to an appropriate length. Next, at block 96, the specimen 12 is mounted on the bracket 24 (FIG. 1).

Proceeding to block 98, the ram 60 is moved to the compressed position and the trigger 80 pivoted to lock the ram 60 in the compressed position.

Continuing to block 100, the horizontal micrometer 42 is manipulated to move the holder 22 toward the ram 60, until the specimen 12 touches the ram wall 66. The reading on the horizontal micrometer 42 is recorded. At block 102, the laser device 26 is engaged with the pins 70, 72, and the vertical micrometer manipulated to move the vertical holder member 50 as appropriate to align the laser device 26 with the paint layer 18 on the specimen 12.

Next, at block 104, the horizontal micrometer 42 is again manipulated to advance the specimen 12 against the ram wall 66, until the desired amount of specimen 12 compression is effected. The readings on both micrometers 42, 52 are recorded.

Then, at block 106, the trigger 80 is pivoted to release the ram 60 to allow the springs 78 to rapidly pull the ram 60 away from the specimen 12. As the specimen 12 is released, it recovers, i.e., it moves toward its relaxed configuration, which causes the paint layer 18 and, hence, reflected laser beam to likewise move. As the reflected laser beam moves across the detector inside the laser device 26, the output of the laser device 26 is processed by the circuit 28 and monitored and recorded by the microprocessor 30.

Concluding the initial test of the specimen 12, at block 108 the laser device 26 is removed from the pins 70, 72, the ram 60 moved back to the compressed position, and the base 20 with specimen 12 heated while compressed and retested using the procedure described above.

FIG. 4 shows the logic followed by the microprocessor 30. When the trigger 80 is released at block 110, digitized data that was generated by the laser device 26 and processed by the circuit 28 is recorded at block 112, until the specimen 12 stabilizes as evidenced by the specimen 12 ceasing movement. Then, at block 114 the actual distance of specimen movement is measured using the horizontal micrometer 42 in accordance with micrometer principles known in the art. This actual distance is input into the microprocessor 30.

Next, at block 116 the microprocessor 30 correlates the voltages from the circuit 28 to the actual distance moved, as determined at block 114. Accordingly, the skilled artisan will appreciate that the fixture 10 is calibrated by the steps above. At block 118, additional tests of the specimen 12 are undertaken, using only the digitized voltage signal from the laser device 26 to determine the distance of specimen 12 movement, and the test results averaged to output a measurement of the movement of the specimen 12 over time as it recovers toward the relaxed configuration.

While the particular WEATHERSTRIP RESILIENCY TEST FIXTURE as herein disclosed and described in detail is fully capable of attaining the abovedescribed objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

We claim:

1. A fixture for testing vehicle weatherstripping, comprising:

a base;

a holder movably disposed on said base for holding the weatherstripping, said holder including an elongated slotted support portion for supporting said weatherstripping; and a ram movably disposed on the base opposite the holder for motion between a compressed position, wherein the ram abuts the weatherstripping to compress the weatherstripping, and a release position, wherein the ram is distanced from the weatherstripping; and a laser device positioned for directing light onto the weatherstripping after said ram is moved to said released position, and for receiving reflected laser light therefrom as said weatherstripping recovers from a compressed configuration to a relaxed configuration.

2. A fixture for determining the resiliency of a specimen of vehicle weatherstripping, comprising:

a holder disposed on a base and including an elongated slotted support portion for supporting said weatherstripping specimen;

a ram movably disposed on the base opposite the holder, the ram being movable to a compressed position, wherein the ram squeezes the weatherstripping specimen against the holder to move the weatherstripping specimen to a compressed configuration, the ram being movable to a release position, wherein the weatherstripping specimen is not compressed against the holder; and a laser device positioned to illuminate the weatherstripping specimen with laser light after said ram is moved to said released position and to detect reflections therefrom as said weatherstripping specimen recovers from a compressed configuration to a relaxed configuration.

3. The fixture of claim 1, further comprising an electric circuit electrically connectable to the laser device for correlating the reflected laser light to distance.

4. The fixture of claim 3, wherein the laser device is engageable with at least one pin coupled to the base, such that the laser device is easily removed from the base to facilitate heating the base with the ram in the compressed position to heat the weatherstripping.

5. The fixture of claim 1, wherein the ram includes:

a ram support fixedly attached to the base, the ram support including at least one ram support rod; and a ram element slidably engaged with the ram support rod for establishing the compressed position and the release position.

6. A fixture for testing vehicle weatherstripping, comprising:

a base;

a holder movably disposed on said base for holding the weatherstripping;

a ram movably disposed on the base opposite the holder for motion between a compressed position, wherein the ram abuts the weatherstripping to compress the weatherstripping, and a release position, wherein the ram is distanced from the weatherstripping; and a laser device positioned for directing light onto the weatherstripping and for receiving reflected laser light therefrom;

wherein said ram includes a ram support fixedly attached to the base, the ram support including at least one ram support rod, a ram element slidably engaged with the ram support rod for establishing the compressed position and the release position, a spring coupled to the ram support and to the ram element to urge the ram element toward the release position, a trigger pivotably mounted on the base and engageable with the ram element for selectively holding the ram element in the compressed position, and a lock engaged with the trigger and movable relative thereto for selectively holding the trigger in engagement with the ram element.

7. A fixture for testing vehicle weatherstripping comprising:

a base;

a holder movably disposed on said base for holding the weatherstripping;

a ram movably disposed on the base opposite the holder for motion between a compressed position, wherein the ram abuts the weatherstripping to compress the weatherstripping, and a release position, wherein the ram is distanced from the weatherstripping; and a laser device positioned for directing light onto the weatherstripping and for receiving reflected laser light therefrom;

wherein the holder includes a horizontal holder member movably disposed relative to the base for moving horizontally toward and away from the ram, a vertical holder member movably disposed relative to the horizontal holder member for vertical motion relative thereto, and a bracket attached to one of the holder members for engaging the weatherstripping.

8. The fixture of claim 7, further comprising horizontal and vertical micrometers respectively engaged with the horizontal and vertical holder members and manipulable by a person for selectively moving the bracket horizontally and vertically, respectively, relative to the base.

9. A method for testing the resiliency of a specimen of vehicle weatherstripping, comprising the steps of:

applying a reflective paint to a portion of said weatherstripping specimen;

disposing the weatherstripping specimen on a base;

compressing the weatherstripping specimen;

juxtaposing a laser with the weatherstripping specimen such that the laser can direct laser light against the reflective paint on said weatherstripping specimen;

releasing the weatherstripping specimen; and detecting laser light reflected from the weatherstripping specimen to detect movement of the weatherstripping specimen as said weatherstripping specimen recovers from a compressed configuration to a relaxed configuration.

10. The method of claim 9, further comprising the steps of:

mounting the specimen on a holder; and movably disposing the holder on the base.

11. The method of claim 10, further comprising the step of:

configuring the holder such that the holder can be adjusted relative to the base in the vertical and horizontal dimensions.

12. The method of claim 11, wherein the compressing step includes:

movably disposing a ram on the base opposite the holder; and compressing the specimen by advancing the ram toward the holder.

13. The method of claim 12, further comprising the step of:

locking the ram in a first position, wherein the specimen is compressed; and releasing the lock to release the specimen.

14. The fixture of claim 2, wherein the ram includes:

a ram support fixedly attached to the base, the ram support including at least one ram support rod; and a ram element slidably engaged with the ram support rod for establishing the compressed position and the release position.

15. The fixture of claim 14, wherein the ram further includes:
- a spring coupled to the ram support and to the ram element to urge the ram element toward the release position;
- a trigger pivotably mounted on the base and engageable with the ram element for selectively holding the ram element in the compressed position; and
- a lock engaged with the trigger and movable relative thereto for selectively holding the trigger in engagement with the ram element.

16. The fixture of claim 15, wherein the holder further comprises:
- a horizontal holder member movably disposed relative to the base for moving horizontally toward and away from the ram; and
- a vertical holder member movably disposed relative to the horizontal holder member for vertical motion relative thereto.

17. The fixture of claim 16, further comprising horizontal and vertical micrometers respectively engaged with the horizontal and vertical holder members and manipulable by a person for selectively moving the bracket horizontally and vertically, respectively, relative to the base.

* * * * *